(12) United States Patent
Kitakawa et al.

(10) Patent No.: US 11,518,778 B2
(45) Date of Patent: *Dec. 6, 2022

(54) METHOD FOR PRODUCING SUGAR FATTY ACID ESTER BY TRANSESTERIFICATION REACTION

(71) Applicant: TOHOKU UNIVERSITY, Sendai (JP)

(72) Inventors: Naomi Kitakawa, Sendai (JP); Tomone Sasayama, Sendai (JP); Ayumu Kanezawa, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/265,666

(22) PCT Filed: Aug. 9, 2019

(86) PCT No.: PCT/JP2019/031715
§ 371 (c)(1),
(2) Date: Feb. 3, 2021

(87) PCT Pub. No.: WO2020/032272
PCT Pub. Date: Feb. 13, 2020

(65) Prior Publication Data
US 2021/0317154 A1    Oct. 14, 2021

(30) Foreign Application Priority Data

Aug. 10, 2018 (JP) .............................. JP2018-152109

(51) Int. Cl.
*C07H 13/06* (2006.01)
(52) U.S. Cl.
CPC .................................. *C07H 13/06* (2013.01)

(58) Field of Classification Search
None
See application file for complete search history.

(56) References Cited

U.S. PATENT DOCUMENTS

| | | | |
|---|---|---|---|
| 4,966,966 A | 10/1990 | Wada et al. | |
| 2019/0185504 A1 | 6/2019 | Kitakawa et al. | |

FOREIGN PATENT DOCUMENTS

| | | | | |
|---|---|---|---|---|
| EP | 0507232 A1 | * | 10/1992 | ............. A01B 63/22 |
| FR | 1 365 067 A | | 6/1964 | |
| GB | 1050452 A | * | 12/1966 | |
| JP | 63-179884 A | | 7/1988 | |
| JP | 05-148285 A | | 6/1993 | |
| JP | 06-122694 A | | 5/1994 | |
| JP | 2008-037847 A | | 2/2008 | |
| WO | 2018/038103 A1 | | 3/2018 | |

OTHER PUBLICATIONS

Eggleston, Journal of Carbohydrate Chemistry, vol. 19, 2000, Issue 9, pp. 1305-1318, abstract only. (Year: 2000).*
Shibasaki-Kitakawa, Bioresource Technology 98 (2007) 416-421. (Year: 2007).*
International Search Report of PCT/JP2019/031715 dated Oct. 29, 2019 [PCT/ISA/210].

* cited by examiner

*Primary Examiner* — Layla D Berry
(74) *Attorney, Agent, or Firm* — Sughrue Mion, PLLC

(57) ABSTRACT

A method for producing a sugar fatty acid ester characterized in that a fatty acid ester and a saccharide are subject to a transesterification reaction using a weakly basic ion exchanger having a $pK_b$ of 3 to 7 as a catalyst.

9 Claims, 1 Drawing Sheet

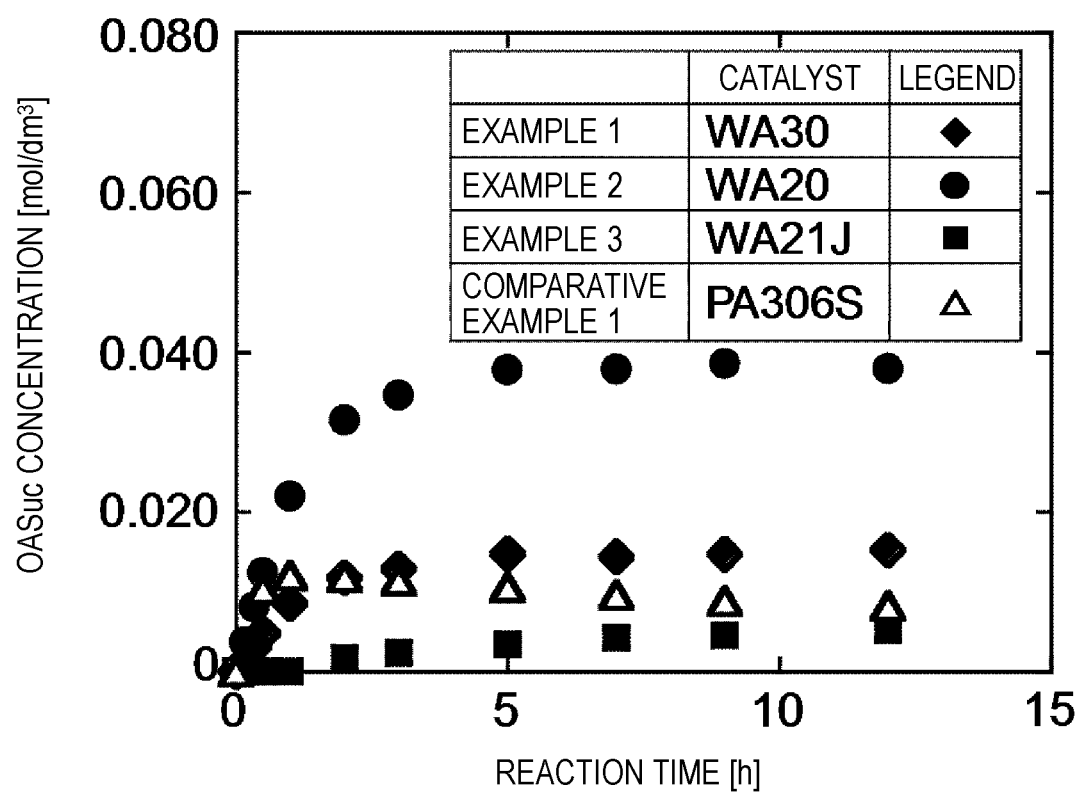

METHOD FOR PRODUCING SUGAR FATTY ACID ESTER BY TRANSESTERIFICATION REACTION

CROSS REFERENCE TO RELATED APPLICATIONS

This application is a National Stage of International Application No. PCT/JP2019/031715, filed Aug. 9, 2019, claiming priority to Japanese Patent Application No. 2018-152109, filed Aug. 10, 2018.

TECHNICAL FIELD

The present invention relates to a method for producing a sugar fatty acid ester by a transesterification reaction between a fatty acid ester and a saccharide. It more specifically relates to a method for producing a sugar fatty acid ester by a transesterification reaction between a fatty acid ester and a saccharide using a weakly basic anion exchanger as a catalyst. The method of the invention can be operated under mild conditions and allows for the production of a sugar fatty acid ester at a high reaction rate.

BACKGROUND ART

High-purity products of sucrose (Suc), a sugar, are available at low cost. Thus, various usages of sucrose as a chemical raw material have been proposed. One of sucrose derivatives currently industrially produced is a sugar fatty acid ester.

A sugar fatty acid ester is a nonionic surfactant having a sugar, which is a hydrophilic group, and a vegetable oil-derived fatty acid, which is a lipophilic group (FA), ester-linked to each other. Such an ester can be changed to hydrophilic or lipophilic depending on the number of fatty acids bonded to a plurality of hydroxyl groups (OH groups) in the sugar, and thus has a wide range of hydrophilic-lipophilic balance (HLB) values. A sugar fatty acid ester has, in addition to an emulsifying ability, high functionality including solubilizing ability, dispersing ability, lubricating ability, and the like.

In addition, in recent years, in the pharmaceutical field, the application of a sugar fatty acid ester as a binder for tablets has been studied, and its utilization in the field of medicines is also expected.

Like this, a sugar fatty acid ester is a high-value-added, biomass-derived chemical product produced from sucrose and a vegetable oil, which are inexpensive, but is known to be difficult to synthesize due to the poor miscibility of a hydrophilic sugar and a fatty acid.

Currently, sugar fatty acid esters are industrially produced from sucrose and a fatty acid alkyl ester (e.g., fatty acid methyl ester) through a transesterification reaction in a homogeneous phase using amphiphilic dimethyl sulfoxide (DMSO) as a solvent and an alkali catalyst as a catalyst. In this method, in order to enhance the conversion, reduced-pressure conditions for removing the by-product methanol are indispensable. In addition, the method is problematic in that a reaction between the fatty acid methyl ester and the catalyst produces soap as a by-product, and also it is difficult to separate the homogeneous alkali catalyst, for example, causing an increase in cost. In order to deal with such problems, for example, a technique in which a reactor including a packed column and a plurality of condensers arranged in series is used, and the condensate in the first-stage condenser is refluxed to the top of the packed column, has been proposed (JP-A-6-122694; PTL 1).

In addition, as a method for producing a sugar fatty acid ester, a method in which sucrose and a lower alkanol ester of a fatty acid or a glyceride are subjected to a transesterification reaction in the presence of a cation exchange resin ion-exchanged with an alkali metal has been disclosed (JP-A-63-179884; PTL 2). However, in a reaction using a strongly basic anion exchange resin having a quaternary ammonium group as a functional group or a weakly basic anion exchange resin having a tertiary amine as a functional group, a sugar fatty acid ester is formed only slightly under reduced pressure conditions, and satisfactory results have not yet been obtained.

The present inventors have proposed a method in which a transesterification reaction between a fatty acid ester and a saccharide is previously carried out through a two-stage process including a step of adsorbing a saccharide onto a resin using a strongly basic anion exchanger and a step of synthesizing a sugar fatty acid ester (WO 2018/038103; PTL 3). This method is advantageous in that it can be implemented at atmospheric pressure, by-product soap is not produced, and it is easy to separate the catalyst, for example. However, a method that uses a strongly basic anion exchanger is problematic in that the decomposition of the formed sugar fatty acid ester may simultaneously proceed, making it difficult to control the reaction, and the production yield is low.

CITATION LIST

Patent Literature

PTL 1: JP-A-6-122694
PTL 2: JP-A-63-179884 (U.S. Pat. No. 4,966,966)
PTL 3: WO 2018/038103 (US Pub. No. 2019-0185504)

SUMMARY OF INVENTION

Technical Problem

Meanwhile, weakly basic solid catalysts are generally used not as catalysts but for the purification of pharmaceuticals or water treatment. PTL 2 states that "all anion exchange resins are basic; however, in the case where the reaction was carried out using a basic anion exchange resin having a quaternary ammonium group as a functional group or a basic anion exchange resin having a tertiary amine as a functional group, satisfactory results were not obtained" (page 11).

An object of the invention is to provide a method for producing a sugar fatty acid ester, according to which the problems with a transesterification reaction using a strongly basic anion exchanger as a catalyst described above, that is, problems in that the decomposition of the product sugar fatty acid ester simultaneously proceeds, making it difficult to control the reaction, and the production yield decreases, for example, have been solved.

Solution to Problem

The present inventors have conducted extensive research on weakly basic anion exchangers. As a result, they have found that when a weakly basic anion exchanger is used as a catalyst, the decomposition of the product is suppressed while maintaining the transesterification reaction ability, whereby the above problems can be solved, and thus accomplished the invention.

The invention relates to a method for a sugar fatty acid ester according to the following [1] to [11].

[1] A method for producing a sugar fatty acid ester, characterized in that a fatty acid ester and a saccharide are subjected to a transesterification reaction using a weakly basic solid catalyst.

[2] The method for producing a sugar fatty acid ester according to the above item 1, wherein the weakly basic solid catalyst is a weakly basic anion exchanger.

[3] The method for a sugar fatty acid ester according to the above item 2, wherein the weakly basic anion exchanger has a $pK_b$ of 3 to 7.

[4] The method for producing a sugar fatty acid ester according to the above item 2 or 3, wherein the weakly basic anion exchanger is a porous-type weakly basic anion exchange resin.

[5] The method for producing a sugar fatty acid ester according to any one of the above items 1 to 4, including a step of adsorbing a saccharide onto a weakly basic solid catalyst (adsorption step) and a step of subjecting the saccharide and a fatty acid ester to a transesterification reaction to synthesize a sugar fatty acid ester (synthesis step).

[6] The method for producing a sugar fatty acid ester according to the above item 5, wherein the adsorption step is a step in which a solution containing a saccharide is supplied to a weakly basic solid catalyst, thereby adsorbing the saccharide onto the weakly basic solid catalyst.

[7] The method for producing a sugar fatty acid ester according to the above item 5, wherein the synthesis step is a step in which a reaction liquid containing a fatty acid ester is supplied to the weakly basic solid catalyst having the saccharide adsorbed thereon in the adsorption step, thereby synthesizing a sugar fatty acid ester.

[8] The method for producing a sugar fatty acid ester according to the above item 7, wherein the reaction liquid containing a fatty acid ester contains a saccharide.

[9] The method for producing a sugar fatty acid ester according to any one of the above items 1 to 8, wherein the fatty acid ester is an ester of a $C_{1-30}$ fatty acid and a $C_{1-8}$ lower alcohol.

[10] The method for producing a sugar fatty acid ester according to any one of the above items 1 to 9, wherein the saccharide is at least one member selected from the group consisting of monosaccharides, disaccharides, and polysaccharides.

[11] The method for producing a sugar fatty acid ester according to any one of the above items 1 to 10, wherein the fatty acid ester is methyl oleate, and the saccharide is sucrose.

Advantageous Effects of Invention

The invention provides a method for producing a sugar fatty acid ester in which a fatty acid ester and a saccharide are subjected to a transesterification reaction using, as a catalyst, a weakly basic anion exchanger whose utilization as a catalyst has not been reported in the past.

According to the invention, (1) a sugar fatty acid ester can be produced at atmospheric pressure without by-production of soap. (2) As a result of using a weakly basic anion exchanger as a catalyst, the decomposition of the product, which proceeds in the case of using a strongly basic ion exchanger as a catalyst, is suppressed. (3) In particular, when a porous-type weakly basic anion exchanger is used, the sugar fatty acid ester yield increases up to about three times that in the case of using a strongly basic anion exchanger, allowing for low-cost production.

BRIEF DESCRIPTION OF DRAWINGS

The FIGURE shows time-dependent changes in the concentration of sucrose oleate (OASuc), which is the product of the transesterification reaction in Examples 1 to 3 and Comparative Example 1.

DESCRIPTION OF EMBODIMENTS

Hereinafter, embodiments of the present invention will be described in detail.

The method for producing a sugar fatty acid ester of the invention is characterized in that a fatty acid ester and a saccharide are subjected to a transesterification reaction using a weakly basic solid catalyst.

[Weakly Basic Solid Catalyst]

A typical example of the weakly basic solid catalyst used in the invention is a weakly basic anion exchanger (in the following description, "weakly basic anion exchanger" and "weakly basic anion exchange resin" are sometimes simply referred to as "anion exchanger" and "anion exchange resin", respectively). The form of the anion exchanger is not particularly limited, and may be granular, membranous, fibrous, or the like.

The weakly basic anion exchanger used in the invention has a base dissociation constant ($pK_b$) within a range of 3 to 7, preferably a $pK_b$ of about 5. As such anion exchangers, commercially available products can be utilized. Specific examples thereof include Diaion WA10, WA20, WA21J, and WA30 (manufactured by Mitsubishi Chemical Corporation), Lewatit MP-62 and VP OC 1065 (manufactured by LANXESS), and Amberlite IRA-478, IRA-68, IRA-96, IRA-98, XE-583, Amberlyst A21, DUOLITE A7, A568, Dowex 66, M-43, Monosphere 66, 77, and Marathon WBA (manufactured by Dow Chemical Company).

With respect to WA30, WA20, and WA21J used in the examples below and a strongly basic anion exchange resin PA306S used in the comparative example (all manufactured by Mitsubishi Chemical Corporation), Table 1 shows the type, functional group, nature (degree of basicity), base dissociation constant ($pK_b$), ion exchange capacity (mol/m³-resin), particle size (mm), and specific surface area (m²/g-resin).

TABLE 1

| | Properties of Anion Exchange Resins | | | |
|---|---|---|---|---|
| Resin | WA30 | WA20 | WA21J | PA306S |
| Type | Highly porous | Porous | Highly porous | Porous |
| Functional Group | Dimethylamine | Polyamine | Polyamine | Trimethylamine |
| Nature | Weakly basic | Weakly basic | Weakly basic | Strongly basic |
| Dissociation Constant ($pK_b$) | 5 to 7 | 5 to 7 | 5 to 7 | <1 |

TABLE 1-continued

Properties of Anion Exchange Resins

| Resin | WA30 | WA20 | WA21J | PA306S |
|---|---|---|---|---|
| Ion Exchange Capacity [mon/m$^3$-resin] | 1500 | 2500 | 2000 | 800 |
| Particle Size [mm] | 0.30 to 1.18 | 0.30 to 1.18 | 0.30 to 1.18 | 0.150 to 0.425 |
| Specific Surface Area [m$^2$/g-resin] | 20 | 1 | 15 | 0.3 to 2.0 |

WA30, WA20, and WA21J are weakly basic. WA20 has a porous-type structure, and WA30 and WA21J have a highly porous-type structure. PA306S is strongly basic and has a porous-type structure. Each resin is based on a gel type, in which particles are internally homogeneous, and the porous type is a resin having a structure in which physical holes (pores) are formed in a gel-type resin. The highly porous type is a resin in which the amount of pores is greater than in the porous type to have an increased specific surface area. With respect to the functional group of each resin, PA306S is a trimethylamine type, WA30 is a dimethylamine type, and WA20 and WA21J are each a polyamine type. The basicity is highest in PA306S, followed by WA30, WA20, and WA21J.

A weakly basic anion exchange resin is in a water-swollen state at the time of purchase (at the time of factory shipment), and a fatty acid ester with low polarity is unlikely to diffuse inside the resin. Thus, in the invention, the resin is swollen with a reaction solvent and then used. In addition, a strongly basic resin at the time of factory shipment is Cl-form, in which functional groups are inactive, and is also in a water-swollen state. Therefore, activation treatments, in which functional group substitution from inactive Cl-form to active OH-form and solvent swelling are performed, are necessary. These treatments can be performed in accordance with the regeneration method for resin recycling built by the present inventors (*Kagaku Kogaku Ronbunshu* (Collection of Papers on Chemical Engineering), 42, 30 to 36 (2016)).

As anion exchange resins, those whose resin backbones have various chemical structures as insoluble carriers can be used. Specific examples thereof include synthetic polymers, such as polystyrene crosslinked with divinylbenzene or the like, polyacrylic acid, crosslinked poly(meth)acrylic ester, and phenol resin, and crosslinks of naturally occurring polysaccharides, such as cellulose. Among them, synthetic polymers are preferable, and crosslinked polystyrene is still more preferable.

In the method of the invention, a fatty acid ester and a saccharide used as raw materials of the transesterification reaction can be selected from any compounds known to those skilled in the art according to the kind of sugar fatty acid ester to be produced, the intended use, and the like. The raw material compounds may be prepared by any methods known to those skilled in the art, and it is also possible to use various kinds of commercially available fatty acid esters and saccharides.

It is possible to use, for example, a lower alcohol having a $C_{1-8}$, preferably $C_{1-5}$, linear or branched hydrocarbon backbone, and, for example, a fatty acid ester composed of a $C_{1-30}$ fatty acid, such as lauric acid, myristic acid, palmitic acid, stearic acid, oleic acid, behenic acid, or erucic acid.

As the saccharide, it is possible to use at least one saccharide selected from monosaccharides, disaccharides such as sucrose, and polysaccharides.

Preferred specific examples of fatty acid esters for use in the method of the invention include methyl oleate used in the Examples, as well as methyl laurate, methyl myristate, methyl palmitate, and methyl stearate, while specific examples of sugars include sucrose.

In the method of the invention, because a lipophilic fatty acid ester and a hydrophilic saccharide are significantly different from each other in polarity and thus poorly miscible, they can be allowed to react with an anion exchange resin in an amphiphilic solvent system known to those skilled in the art, such as dimethyl sulfoxide, dimethyl formamide, ethyl methyl ketone, ethyl acetate, 2-propanol, propylene glycol, methanol, ethanol, and 2-methyl-1-propanol.

In the method of the invention, it is preferable that a saccharide is previously substantially adsorbed onto a weakly basic anion exchange resin and then used. For example, it is preferable that the method is implemented through the following two steps: a step in which, prior to a transesterification reaction between a fatty acid ester and a saccharide, a saccharide is substantially adsorbed onto a weakly basic anion exchange resin (adsorption step), and a subsequent step in which using the anion exchange resin obtained in the adsorption step, a fatty acid ester and the saccharide are subjected to transesterification reaction to synthesize a sugar fatty acid ester (synthesis step).

The contact between the reactant and the anion exchange resin in each step may be made in any style known to those skilled in the art, such as a batch method (batch system) or a continuous method (distribution system). As the form of the apparatus, one equipped with a treatment tank, one in which the resin is transferred through a circulation system or a countercurrent system, and the like can be mentioned. As the contact method, distribution (method in which a liquid is passed through a packed bed or fluidized bed of an ion exchange resin), stirring (method in which a stirring tank is used), shaking (shaking-type reactor), and the like can be mentioned. It is also possible to use a column pass-through type, in which the introduction port for a raw material to be supplied and the recovery port for a product are fixed, or an expanded bed (expanded bed column). In addition, a batch type can also be used.

Incidentally, in a batch method (batch system), the reactant concentration decreases with the progress of the reaction. Therefore, in the case where it is difficult to keep the saccharide concentration high, reactants can be added as necessary.

Meanwhile, in a continuous method (distribution system) using a reactor packed with a resin, it is preferable to maintain the high saccharide concentration because, as a result, the target sugar ester synthesis reaction can preferentially proceed.

In the case of employing a continuous method (distribution system), it is preferable that as a first stage, a step in which a reaction liquid containing a saccharide is supplied to an anion exchange resin to adsorb the saccharide (adsorption step) is performed, and then, as a second stage, a step in which a reaction liquid containing a fatty acid ester alone or a fatty acid ester and a saccharide is supplied to the anion exchange resin to cause a transesterification reaction between them, thereby synthesizing a sugar fatty acid ester (synthesis step), is performed. In particular, during the synthesis step, it is preferable that a reaction liquid containing a fatty acid ester and a saccharide is supplied so that the saccharide in the anion exchange resin, which is a catalyst, is maintained at a high concentration, thereby enhancing the saccharide concentration in the reaction liquid.

The saccharide concentration (molar concentration ratio of a saccharide to a fatty acid ester) in the reaction liquid used in the synthesis step is preferably within a range of 1:0.5 to 1:5, and more preferably within a range of 1:0.5 to 1:3. In the case where the molar concentration ratio of the saccharide is less than 0.5, it may happen that the catalytic activity of the anion exchange resin disappears, and, even when a saccharide is introduced into the anion exchange resin thereafter, a transesterification reaction with the fatty acid ester does not occur efficiently. Meanwhile, in the case where the molar concentration ratio of the saccharide is more than 5, the concentration of the reaction liquid becomes too high, and this also causes an increase in cost, which is undesirable in terms of productivity. In addition, when a saccharide is added too much, an operation for saccharide removal from the product is needed, deteriorating the productivity.

In order to achieve the desired object in the method of the invention, the operations of the above two steps may be combined with any production process. For example, a step of separating/purifying a sugar fatty acid ester, which is the target product, from an alcohol, which is a non-target product, other impurities, and the like may further be included. That is, in the method for producing a sugar fatty acid ester using a weakly basic anion exchanger as a catalyst of the invention, the composition resulting from a transesterification reaction between a fatty acid ester and a saccharide is a composition in which the product (sugar fatty acid ester) and unreacted reactants (saccharide or fatty acid ester) are contained, or a composition in which an alcohol and the like are contained, in the solvent. In order for the product sugar fatty acid ester to be acquired and purified from such a composition, an extraction step and a water washing step are repeated a desired number of times, and the extracting solvent is distilled off from the extract, followed by drying, whereby a product-containing mixture containing no solvent can be obtained. From this product-containing mixture, a high-purity sugar fatty acid ester can be obtained through any known technique incorporating, for example, a distillation step, a membrane separation step, a preparative liquid chromatography separation step, and the like.

Other conditions and techniques in the method of the invention, such as the molar concentration and the molar ratio of each reactant, the amount of anion exchange resin used, the quantitative ratio between the anion exchange resin and the reactant, the temperature/pressure in the reaction system, and the reaction time, can be suitably selected from any known ones in consideration of the kind of each reactant and anion exchange resin used, for example. For example, the reaction time in each step can be suitably set according to the reaction temperature, the amount of anion exchange resin used, and the like. The reaction is usually carried out at 20 to 100° C., preferably 30 to 70° C. The reaction pressure is not particularly limited. Although a reaction at atmospheric pressure is easy in operation, as necessary, the pressure may be increased to about 1 to 10 atm or reduced to about 0.002 to 1 atm.

EXAMPLES

Hereinafter, the synthesis of sugar fatty acid esters will be described with reference to examples and a comparative example. However, the invention is not limited to the following description.

Reaction Raw Materials:

Methyl oleate (sometimes abbreviated to OAMe) <manufactured by FUJIFILM Wako Pure Chemical Corporation> was used as a fatty acid ester, and sucrose (sometimes abbreviated to Suc) (manufactured by FUJIFILM Wako Pure Chemical Corporation) was used as a sugar.

Solvent: As in the industrial production method, dimethyl sulfoxide (DMSO) was used.

Catalyst: Commercially available four kinds of porous resins (manufactured by Mitsubishi Chemical Corporation) were used. The type, functional group (functionality), nature (degree of basicity), $pK_b$, ion exchange capacity ($mol/m^3$), particle size (mm), and specific surface area ($m^2/g$) of each resin are as shown above in Table 1.

Pretreatment of Catalyst:

A weakly basic anion exchange resin was swollen with a reaction solvent and then used. In addition, a strongly basic resin was subjected to activation treatments in accordance with the Examples of PTL 3, in which functional group substitution to active OH-form and solvent swelling were performed, and then used.

Reaction Conditions:

In the synthesis using a weakly basic resin (Examples 1 to 3), the pretreated resin was brought into contact with a DMSO solution containing 0.66 $mol/dm^3$ of Suc to sufficiently adsorb Suc. Next, the resin was fed to a reaction liquid containing 0.30 $mol/dm^3$ of Suc and 0.10 $mol/dm^3$ of OAMe to a moisture mass of 20 mass %, and sufficiently shaken at 60° C. to cause a reaction.

The synthesis using a strongly basic resin (Comparative Example 1) was performed in accordance with the Examples of PTL 3.

In each experiment, the OASuc concentration in the product was measured using liquid chromatography with an evaporative light scattering detector. In addition, in order to check the mass balance before and after the reaction, the Suc concentration was measured using liquid chromatography with an evaporative light scattering detector, while the OAMe concentration was measured using liquid chromatography with an ultraviolet-visible spectroscopic detector.

The experiment conditions, maximum OASuc concentration, and maximum OASuc yield are collectively shown in Table 2.

TABLE 2

Experiment Conditions and Results

| | Example 1 | Example 2 | Example 3 | Comparative Example 1 |
|---|---|---|---|---|
| Resin | WA30 | WA20 | WA21J | PA306S |
| Amount of Catalyst [wt %] | 20 | 20 | 20 | 20 |
| Initial Suc Concentration [$mol/dm^3$] | 0.30 | 0.30 | 0.30 | 0.30 |

TABLE 2-continued

Experiment Conditions and Results

| | Example 1 | Example 2 | Example 3 | Comparative Example 1 |
|---|---|---|---|---|
| Initial OAMe Concentration [mol/dm$^3$] | 0.10 | 0.10 | 0.10 | 0.10 |
| Temperature [° C.] | 60 | 60 | 60 | 60 |
| Maximum OASuc Concentration [mol/dm$^3$] | 0.015 | 0.039 | 0.0051 | 0.014 |
| Maximum OASuc Yield [%] | 15 | 39 | 5.1 | 14 |

[Results]

The FIGURE shows time-dependent changes in the OASuc concentration in the product in Examples 1 to 3 and Comparative Example 1. In Comparative Example 1 (Δ) using a strongly basic ion exchange resin PA306S, the OASuc concentration increased after the start of the reaction and gradually decreased after reaching the maximum concentration. This is presumably attributable to the decomposition of the formed OASuc. Meanwhile, in Examples 1 to 3 using a weakly basic ion exchange resin, in each case, the OASuc concentration slowly increased and then became constant. The maximum value of the OASuc concentration increased in the following order: WA21J (■)<WA30 (♦)<WA20 (●). In WA20 with the highest maximum, the value was 2.8 times the maximum concentration in Comparative Example 1 using a strongly basic ion exchange resin PA306S. The mass balance before and after the reaction in the case of using a weakly basic ion exchange resin was checked. As a result, it became clear that the decomposition of the product OASuc did not occur.

The invention claimed is:

1. A method for producing a sugar fatty acid ester, characterized in that a fatty acid ester and a saccharide are subjected to a transesterification reaction using a weakly basic solid catalyst, comprising a step of adsorbing a saccharide onto a weakly basic solid catalyst (adsorption step) and a step of subjecting the saccharide and a fatty acid ester to a transesterification reaction to synthesize a sugar fatty acid ester (synthesis step), wherein the absorption step is conducted in advance of the esterification reaction (synthesis step) and
wherein the adsorption step is a step in which a solution containing a saccharide is supplied to a weakly basic solid catalyst, thereby adsorbing the saccharide onto the weakly basic solid catalyst.

2. The method for producing a sugar fatty acid ester according to claim 1, wherein the weakly basic solid catalyst is a weakly basic anion exchanger.

3. The method for a sugar fatty acid ester according to claim 2, wherein the weakly basic anion exchanger has a pK$_b$ of 3 to 7.

4. The method for producing a sugar fatty acid ester according to claim 2, wherein the weakly basic anion exchanger is a porous-type weakly basic anion exchange resin.

5. The method for producing a sugar fatty acid ester according to claim 1, wherein the synthesis step is a step in which a reaction liquid containing a fatty acid ester is supplied to the weakly basic solid catalyst having the saccharide adsorbed thereon in the adsorption step, thereby synthesizing a sugar fatty acid ester.

6. The method for producing a sugar fatty acid ester according to claim 5, wherein the reaction liquid containing a fatty acid ester contains a saccharide.

7. The method for producing a sugar fatty acid ester according to claim 1, wherein the fatty acid ester is an ester of a C$_{1-30}$ fatty acid and a C$_{1-8}$ lower alcohol.

8. The method for producing a sugar fatty acid ester according to claim 1, wherein the saccharide is at least one member selected from the group consisting of monosaccharides, disaccharides, and polysaccharides.

9. The method for producing a sugar fatty acid ester according to claim 1, wherein the fatty acid ester is methyl oleate, and the saccharide is sucrose.

* * * * *